United States Patent [19]

Teschemacher et al.

[11] Patent Number: 4,681,871

[45] Date of Patent: * Jul. 21, 1987

[54] PHARMACOLOGICALLY ACTIVE PEPTIDES

[76] Inventors: Hansjorg Teschemacher, Universitat Giessen Frankfurterstr. 107, 6300 Giessen 1; Victor Brantl, Frauenplatz 10, 8000 Munchen; Agnes Henschen; Friedrich Lottspeich, both of Max Planck Institut fur Biochemie, 8033 Martinsried, all of Fed. Rep. of Germany

[*] Notice: The portion of the term of this patent subsequent to Jun. 28, 2000 has been disclaimed.

[21] Appl. No.: 229,577

[22] PCT Filed: May 20, 1980

[86] PCT No.: PCT/DE80/00072

§ 371 Date: Jan. 25, 1981

§ 102(e) Date: Jan. 22, 1981

[87] PCT Pub. No.: WO80/02696

PCT Pub. Date: Dec. 11, 1980

[30] Foreign Application Priority Data

May 25, 1979 [DE] Fed. Rep. of Germany ....... 2921216

[51] Int. Cl.$^4$ .................. A61K 37/02; C07K 5/08; C07K 5/10; C07K 7/06

[52] U.S. Cl. .................. 514/15; 514/16; 514/17; 514/18; 530/328; 530/329; 530/330; 530/331

[58] Field of Search .............. 260/112.5 R; 424/177; 530/302, 328, 329, 330, 331; 514/15, 16, 17, 18

[56] References Cited

U.S. PATENT DOCUMENTS

| | | | |
|---|---|---|---|
| 3,793,304 | 2/1974 | Wieland et al. | 424/177 |
| 4,028,318 | 6/1977 | Aurell et al. | 260/112.5 R |
| 4,119,620 | 10/1978 | Nagatsu et al. | 260/112.5 R |
| 4,247,454 | 1/1981 | Af Ekenstan et al. | 260/112.5 R |
| 4,252,715 | 2/1981 | Aurell et al. | 260/112.5 R |
| 4,254,106 | 3/1981 | Wilkinson | 530/302 |
| 4,390,527 | 6/1983 | Brantl et al. | 530/302 |

FOREIGN PATENT DOCUMENTS

| | | | |
|---|---|---|---|
| 2328093 | 12/1973 | Fed. Rep. of Germany | 424/177 |
| 2298334 | 8/1976 | France | 424/177 |
| 48-43906 | 12/1973 | Japan | 424/177 |

OTHER PUBLICATIONS

Unlisted Drugs, Feb. 1980, edit Spec. Library Association, Naunym Schmied Arch. Pharmacol 308 (Suppl.): R39 (155 Abs), 1979 Casomorphins siehe Zusammenfassung.

*Primary Examiner*—Delbert R. Phillips
*Attorney, Agent, or Firm*—Marshall, O'Toole, Gerstein, Murray & Bicknell

[57] ABSTRACT

Pharmacologically active peptides with opiate-like activity are provided having stability to proteases. The products can be obtained by enzymatic digestion of casein.

The active peptides have the grouping Tyr-Pro-A where Tyr is tyrosine, Pro is proline and A is any amino acid group.

11 Claims, No Drawings

PHARMACOLOGICALLY ACTIVE PEPTIDES

The invention deals with new pharmacologically active peptides, in particular, peptides with opiate-like activity, methods for their activation and/or isolation, methods for their synthetic manufacture, as well as pharmacologically active peptides manufactured according to these methods.

Pharmacologically active peptides have been known which in special biological testing systems display a specific opiate-like activity. They are, in particular, those pentapeptides isolated from the brain by Hughes et al. (Nature 258, 577, 1975): methionine cephalin and the leucine cephalin as well as their longer chain analogs. These known peptides and their synthetic derivatives have the disadvantage that they lose their pharmacological activity, in this case an opiatelike activity, after treatment in vitro with proteases (for example, Pronase E.Merck) after a short incubation period. On in vivo administration these peptides are only slightly attacked and destroyed by proteases naturally present in the body.

It is an object of the present invention to create new pharmacologically active peptides, in particular, ones with opiate-like activity, which have a new, special amino acid sequence, and which have, based on this sequence, a surprisingly increased stability against the peptide-splitting enzymes (proteases, for example, Pronase E. Merck). It is furthermore an object of the invention to put those skilled in the art in a position so they can manufacture the peptide in any desired amount using customary methods, by disclosing the amino acid sequence of the pharmacologically active peptides.

This object is satisfied according to the invention in that the pharmacologically active peptides have the following formula: Tyr-Pro-A-Pro-B-Pro-C-Pro-D . . . etc., in which Tyr is equal to the amino acid tyrosine, and Pro is equal to the amino acid proline. A, B, C, D, . . . etc., can be any amino acid (also Pro/Tyr).

According to a further development of the invention, one of the peptide chain ends has the grouping Tyr-Pro-A-Pro-B-Pro-C-Pro-D . . . etc., in which the proline residues have been entirely or partially substituted by amino acid residues of tryptophan, leucine, alanine, glycine, isoleucine, tyrosine, phenylalanine, valine, histidine, hydroxyproline, asparagine and/or methionine. A, B, C, D . . . etc., can be any amino acid.

According to an advantageous further development, the pharmacologically active peptides have the following formulas:
Tyr-Pro-A
Tyr-Pro-A-Pro
Tyr-Pro-A-Pro-B
Tyr-Pro-A-Pro-B-Pro
Tyr-Pro-A-Pro-B-Pro-C
Tyr-Pro-A-Pro-B-Pro-C-Pro
Tyr-Pro-A-Pro-B-Pro-C-Pro-D . . . etc.
A, B, C, D can be any amino acid, including Pro and Tyr.

According to a particularly advantageous further development the letters, A, B, C, D of the peptides listed up to now are:
A: phenylalanine
B: glycine
C: isoleucine
D: asparagine According to another further development, the optically-active amino acids and/or amino acid residues of the peptides have been replaced by those which have a D-, L-or D/L stereochemical configuration.

According to a preferred further development, all amino acids of the peptide are present in L-form.

According to another further development (a) the end-positioned tyrosine has the general formula:

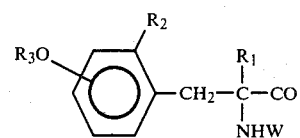

and is substituted by:

$R_1$ for hydrogen or an alkyl group with 1 to 4 C-atoms, $R_2$ for hydrogen or together with $R_1$ for an ethylene bond, $R_3$ for hydrogen, an alkyl group with 1 to 4 C-atoms or an $R_4CO$-group, $R_4$ for a saturated or unsaturated straight or branched chain alkyl residue with 1 to 17 C-atoms, a phenyl residue or a phenyl alkyl residue with 7 to 12 C-atoms, whereby the phenyl residues can be substituted by 1 or 2 substitutents from the halogen series, alkyl with 1 to 4 C-atoms or alkoxy with 1 to 4 C-atoms, whereby the $R_3O$-group is in the meta position or para position to

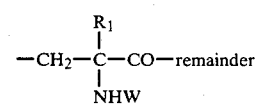

W for the hydrogen, alkyl with 1 to 5 C-atoms, alkenyl with 3 to 5 C-atoms, cyclopropylmethyl, cyclobutylmethyl, $R_4CO$-, H-Lys-, H-Phe- or H-Tyr.

(b) The phenylalanine of the general formula:

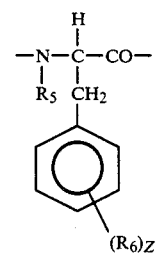

is substituted by:

$R_5$ for hydrogen or alkyl with 1 to 4 C-atoms, $R_6$ for hydrogen, fluorine, chlorine, bromine, nitro, alkyl with 1 to 4 C-atoms or alkoxy with 1 to 4 C-atoms, Z for one or two substituents.

(c) the proline of the general formula:

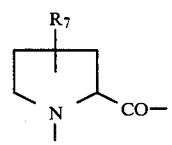

is so modified that:

R$_7$ stands for hydrogen, a hydroxy group, an alkyl group or an alkoxy group with 1 to 4 C-atoms, that at the nitrogen, an alkyl group or an alkoxy group with 1 to 4 C-atoms is bound, one or several keto groups are positioned in the ring.

(d) the end-positioned, C-terminal amino acid is an amide or an ester.

The peptides according to the invention have an advantageous as well as a surprising stability to proteases. This stability to proteases presumably can be partially or entirely attributed to the introduction of the amino acid proline into the peptide chain; thus, attack by the proteases is hindered. This stability to proteases can be especially advantageous for pharmacological applications, since one can obtain a longer action with smaller doses.

Another advantage of the pharmacologically active peptides according to the invention is the controlability of their pharmacological effectiveness, which here is opiate-like, over the chain length; thus, the peptide according to the invention with five amino acids is considerably more effective than that with seven amino acids, with reference to the molar concentration of the substances in comparison to normorphine (see example of the embodiment). Thus it is possible, via the peptide chain length, to "tailor" a desired effect.

According to a further development of the invention the peptides according to the invention are created from natural sources by using customary methods and then isolated. The pharmacologically active peptides can be released from animal and vegetable proteins by means of enzymes and thus be activated.

According to a further development, the pharmacologically active peptides from α and/or β and/or κ casein are released by enzymes and activated. This is especially advantageous since neither the casein itself nor its chloroform/methanol (65/35, vol/vol) extracts, shows a pharmacological, in this case an opiate-like, activity.

According to a particularly preferred further development the enzymes used are of pancreatic origin.

According to another advantageous embodiment of the invention the enzymes trypsin, chymotrypsin, Pronase E, thermolysin, individually and/or mixtures thereof, are used.

A characteristic feature of the invention is that the release of the pharmacologically active peptides by the above-mentioned enzymes is accompanied with only slight, or no, simultaneous attack by the enzymes on the peptides.

According to a further development of the invention the pharmacologically active peptides are separated from an enzymatically digested casein by means of one or more of the following steps:

(a) an extraction with chloroform/methanol (65/35; vol/vol)

(b) adsorption of the evaporated chloroform/methanol extract from aqueous solution on activated carbon.

Desorption with pure chloroform.

(c) adsorption of the evaporated chloroform extract from aqueous solution on Amberlite® (XAD-2, 300–1000 mesh).

Desorption by means of methanol.

(d) further purification of the methanol extract by means of a high pressure liquid chromatography apparatus (HPLC) via a so-called "reversed phase" column (filling material: μ-Bondapak C$_{18}$, Waters) and via a silica gel column (filling material: μ-Porasil, Waters) in lipophilic and/or hydrophilic solvents.

(e) chromatography on a Biogel P 2 column.

The enzymatic casein-hydrolyzate used can be Serva C/TLG 16300 and/or C/PLB 16322. Here we would like to state that other casein hydrolyzates, for example, Serva C/HSF 16320 and C/HSH 16322 do not contain any extractable pharmacologically effective peptides.

The opiate-like activity can be increased by means of incubation with carboxypeptidase (see example of the embodiment).

According to a further development of the invention the pharmacologically active peptides according to the invention are synthesized with a method common in peptide chemistry and/or in nature.

By customary methods is understood the introduction as well as the splitting-off of protective groups (for example: the protection of the amino group by carbobenzoxychloride; the protection of acid groups as an ester) during the synthesis. Also customary are syntheses on carrier substances like, for example, polystyrene.

According to a further development of the invention the pharmacologically active peptides are formed by creating the peptide bond between individual amino acids and/or smaller peptide fragments by means of customary methods.

The pharmacologically active peptides according to the invention according to one of the claims 1 to 16, and/or their derivatives and/or their salts can be contained in human and animal medicaments. These can find use, in particular, as antitussives, antidiarrhetics, analgetics, antipsychotics and tranquilizers.

According to a further development of the invention the peptides characterized in claims 1 to 16 are used as diagnostics.

They can, for example, in an analysis for opiate-like active substances in milk and/or its products, serve as an indicator of microorganism attack.

According to a further development of the invention the peptides according to the invention according to claims 1 to 16, after bonding the thyreoglobulin or other macromolecular albumen bodies, are used as antigens for the formation of antibodies, in mammal organisms, against the peptides described in the claims 1 to 16, and the concentration of these antibodies in the body tissues and body fluids determined by analysis.

The peptide can also be bonded in a customary manner with carbodiimide and the macromolecule injected subcutaneously into the skin of the back and belly of a rabbit.

According to a further development of the invention the derivatives of the peptides according to the invention, according to claims 1 to 7, can be used as opiate antagonists.

EXEMPLIFIED EMBODIMENTS

The disclosed invention is illustrated by means of the following two examples. The first describes the isolation of a heptapeptide with opiate-like activity from enzymatically split casein. The second describes the total synthesis of an opiate-like active pentapeptide.

EXAMPLE I

Isolation of a heptapeptide with opiate-like activity from enzymatically split casein.

All supernates and filtrates from the extraction procedures and adsorption procedures described in the following, as well as all fractions from the high pressure liquid chromatography, and from the gel filtration were tested with respect to their content of opiate-like active substances by means of a process which will be subsequently described.

Step 1: Chloroform/methanol extraction 442 g of a beef casein peptone (casein split products after enzyme treatment, Serva, C/TLG 16300) was mixed with about 3 liters of chloroform/methanol (65/35, v/v) and this suspension was stirred overnight by means of a magnetic stirrer.

(This and the following purification steps were carried out at room temperature). The suspension was thereafter filtered through plaited paper filters (Schleicher - Schuell) and the filtrate then was dried by means of a rotary evaporator.

Step 2: Activated carbon adsorption

The evaporation residue from Step 1 was mixed with activated carbon (No. 2186, Merck) (weight ratio 1:1) and this mixture was suspended in water (1/6, weight/volume). After stirring for ten minutes the suspension was centrifuged and the supernate was removed. The sediment from this centrifugation was resuspended in water; this suspension again was centrifuged and the supernate was removed again. This step, including the resuspension, centrifugation and the removal of the supernate thereupon was again repeated twice, however, using methanol. The desorption of the opiate-active peptide from activated carbon was done by repeating the described procedure twice using chloroform. The chloroform supernate was filtered through filter paper and the filtrate was evaporated on a rotary evaporator. The residue was put into a small volume of chloroform/methanol (1/1, v/v) and filtered through a microfilter (No. FHLPO - 1300 Millipore) in order to remove the activated carbon residues; the filtrate was evaporated.

Step 3: Amberlite ® XAD-2-adsorption

The evaporation residue according to Step 2 was put into water (1/10, weight/volume). To this solution was added Amberlite ® XAD-2-resin (300/1000 mesh, Serva) in the ratio (10/5, volume/weight). After ten minutes of stirring the suspension was filtered through filter paper. The residue which contained the Amberlite ® resin, on which the opiate-active peptide was adsorbed, was washed with a large volume of water (1/25, weight/volume) by means of filtration and the filtrate was rejected. The Amberlite ® XAD-2-resin was suspended in methanol (1/5, weight/volume), the suspension was filtered and the filtrate which contained the opiate-active peptide was evaporated on the rotary evaporator.

Step 4: High pressure liquid chromatography (HPLC)

A Waters chromatograph (Waters, Millford, Mass.) equipped with two pumps (6000 A), a gradient programmer apparatus (660) and a UV-detector/254 nm (440) were used during the following steps. All samples were filtered prior to the injection into the HPLC system by means of micro filters (Millipore). The injection volumes amounted to 100–300 microliters. Only solvents of p.a. quality were used. The eluates were collected in fractions of one or two milliliters. After evaporation of the fractions on the rotary evaporator, or after their lyophilization, the respective residues were put into water and their opiate-like activity was tested. The fractions of material with opiate-like activity from one HPLC purification step were united, freeze-dried and further treated in the steps described hereafter. The columns used during the HPLC, after each run, were washed with 100% of methanol. In order to avoid overloading of the columns with sample material, the material from a specific purification step was chromatographed in up to ten separate individual runs, and the fractions, from the individual runs, which showed opiate-like activity were united again for the next step.

HPLC/Step 1: The material with opiate activity from Step 3 was put in 0.1N acetic acid/methanol (1/1, v/v) and put on a μ-Bondapak C 18 column (internal diameter 7.9 mm; length 30 cm) and elutriated with 0.1N acetic acid/methanol. The elution rate amounted to 2.5 ml/min. The opiate activity was elutriated between 6 and 11 min.

HPLC/Step 2: The material with opiate activity from Step 1 was put into ethanol/water (3/97, v/v) and again placed on a μ-Bondapak C 18 column. Ethanol/water (3/97, v/v) served as eluent. The flow speed amounted to 3 ml/min. Within a time of 30 min. no opiate activity was elutriated. Only in the following linear 20 minute gradient of ethanol/water (3/97, v/v) on 100% of ethanol, an opiate activity could be ascertained in the fractions, which were collected within the 12th and 13th minute after the start of the gradient.

HPLC/Step 3: The opiate active material of Step 2 was freeze-dried, put into a small amount of chloroform/methanol (1/1, v/v) and placed on a Microporasil column (internal diameter 7.9 mm; length 30 cm). Chloroform/methanol (1/1, v/v) served as eluent at a flow speed of 2.5 ml/min. The opiate activity was elutriated between 5.5 and 8.5 min.

HPLC/Step 4: The opiate active material from Step 3 was put into water and put on the Microporasil column. During a 10 minute chromatography and using water as eluent (flow speed 2.5 ml/min), no opiate activity was elutriated. After this a 10/min linear gradient of 100 percent water was driven onto 100% of methanol. Opiate active material which was elutriated over the entire span of the gradient was pooled, rotated and the liquid component freeze-dried.

HPLC/Step 5: The opiate-like active material elutriated in the gradient of Step 4 was put into water/methanol (1/1, v/v) and placed on the Microporasil column and elutriated with this eluent at a flow speed of 2.5 ml/min. The elution time of the opiate activity amounted to 5.7 to 7.2 min.

Step 5: Gel Filtration

The opiate-like active material of the last HPLC step was placed on a BIO-GEL P 2 column (−400 mesh) (internal diameter 1.0 cm; length 135 cm) and elutriated with trifluoroacetic acid/water (0.04%, v/v). The flow speed amounted to 5.5 ml/hr. The UV absorption of the eluate was measured at 220 and 280 nm wave length and registered. The elution volume of the opiate active material was between 79 and 84 ml. The UV absorption showed a sharp peak at this point of 220 and 280 nm. The specific activity of the elutriated material amounted to 6500 nanomole normorphine-equivalent (per g). A post-purification was not able to increase the specific activity.

Proof of the Opiate-Like Activity of the Partially or Completely Purified Compounds All supernates and filtrates from the extraction procedures and the adsorption procedures, as well as all fractions from the high pressure liquid chromatography, and from the gel filtration, were tested with respect to their opiate-like activity using a longitudinal muscle plexusmyentericus preparation of guinea pig ileum. The samples for this purpose had been previously either evaporated or freeze-dried. After putting the products into water, portions of these samples were added to the organ bath and tested for their restricting effect on electrically stimulated contractions of the guinea pig intestine preparation. The restricting effect of the substances to be tested was considered as opiate-specific, when they were neutralized after adding the specific opiate-antagonist naloxon and when, after additional adding of naloxon, no restriction by the sample was any longer caused. Preparation and electrical stimulation of the guinea pig intestine were carried through (frequency 0.1 hz, pulse 60 V, 0.5 ms) as described by Kosterlitz et al. (Kosterlitz, H. W.; Lydon, R. J.; and Watt, A. J., *Brit. J. Pharmacol.* 39, 398–413 (1970) and Schulz and Goldstein (Schulz, R.; and Goldstein, A. J., *Pharmacol. Exp. Ther.* 183, 404–410 (1972).

For controlling the effectiveness of the various purification steps, the specific opiate-activity was determined: for this the opiate-like activity of the various samples per unit weight was determined, and this activity was compared to the activity of the opiate normorphine, which had been respectively tested, under the same conditions as the sample, on the guinea pig intestine. The quantitative data resulting from this are thus given in nanomoles (n mol.) normorphine equivalents.

Characteristic Features of the Isolated Peptides with Opiate-Like Activity

The opiate-active material from the last purification step (gel filtration) was heated with 6N HCl for 24 hours under vacuum, in order to split the peptide. An amino acid analysis with a commercial amino acid analyzer (Biotronik) of the hydrolized material resulted in Tyr: 0.9; Pro: 2.7; Phe: 1.0; Gly: 1.1; Ile: 0.8. This result corresponded to the theoretical values of the amino acid sequence of the β-casein chain: Tyr: 1; Pro: 3; Phe: 1; Gly: 1; Ile: 1. The numbers refer to the residues per mole of peptide. A N-terminal reduction with phenylmustard oil according to Edmann (Edmann, P. and Henschen, A. (1975) in: Protein Sequence Determination, Needleman, S. B., ed., 2$^{nd}$ Edition, pages 232–279, Springer-Verlag, Berlin) resulted in the sequence: Tyr-Pro-Phe-Pro-Gly-Pro-Ile. This heptapeptide received the name β-casomorphin-7. An incubation of 3 mg of the β-casomorphin-7 with 0.2 mg carboxy peptidase (Type Y, Boehringer) at 37° C. in 6 molar (M) acetate buffer at pH 5.5 led to a massive increase in the opiate activity during the first three hours. Thus by means of carboxy peptidase influence, by means of the reduction of the peptide from the C-terminal side, a shorter activated fragment was created. An elution of the BIO-GEL P 2 column which had been used in Step 5, resulted in three main components: Residues of the initial material (β-casomorphin-7) eluted between 79 and 84 ml; after 95 to 100 ml a material was eluted having a specific opiate activity which was higher by a factor of 10 to 20 than that of β-casomorphin-7, and then a third material called β-casomorphin-3 was obtained by further elution.

A hydrolysis of the second material eluted from the column and a subsequent reduction according to Edmann (see above) resulted in the sequence Tyr-Pro-Phe-Pro-Gly. This newly created pentapeptide received the name β-casomorphin-5.

As proof of the resistance against proteases we would like to cite an example: 0.3 mg β-casomorphin-7 was incubated in 0.6 ml tris-buffer pH 8 with 0.02 mg Pronase E (Merck) at 37° C. for 1 to 4 hours. After the end of the incubation, the mixture, for the purpose of destroying the Pronase, was heated at 95° C. for 15 minutes. A comparison with the control sample without the addition of the enzyme did not result in any loss of opiate activity in the subsequent opiate test, while a sample with enzyme and methionine-enkephalin completely lost the opiate activity.

Further Opiate-Characteristics of the Peptides According to the Invention

The opiate characteristics of the peptides according to the invention include, besides the activity on isolated organs and their preparations (guinea pig intestine), also activity on the central nervous system. This becomes obvious from a test, in which those peptides were injected into the ventricle system of rats. Thirty to 45 minutes after the injection of 400 to 1200 micrograms (dissolved in 10 microliters) of a peptide according to the invention (β-casomorphin-7) into the ventricular system, the rats showed a severe analgesia (reduced pain sensitivity) which, after subcutaneous injection of 10 mg per kg body weight of the specific opiate antagonist naloxon, was neutralized.

EXAMPLE II

Synthesis of a pentapeptide according to the invention having the sequence: Tyr-Pro-Phe-Pro-Gly-methyl-ester.

A. Synthesis plan: The amino component is transformed at −15° C. or lower in dimethylformamide (DMF) with a 0.5 molar surplus of mixed anhydride of a Z-amino acid-isobutylcarboxylic acid (whereby Z serves as a protective group and represents an N-benzyloxycarbonyl residue) in 2 to 4 hours.

The mixed anhydride is formed in DMF at −15° C. or lower in 10 to 15 min. by using a 6% surplus of Z-amino acid derivative and N-methylmorpholine via the known chlorine-formic acid-isobutyl ester system. The surplus of mixed anhydride then is destroyed. At 0° C. the pH of the reaction product is set at 8 with an aqueous, saturated $KHCO_3$ solution and stirred for 30 min. at 0° C.

The peptides were extracted with ethyl acetate. The ethyl acetate-peptide mixture, in order to remove the Z-amino acid potassium salt, was washed three times with sodium chloride/water, and three times with water, and evaporated. The peptide which was thus obtained and which still carries the protective group Z, was hydrated in methanol. Then 100 to 500 mg Pd/activated carbon catalyst per mmol peptide were added. The $CO_2$ splitting was controlled with a $Ba(OH)_2$ solution. The catalyst was filtered out (Schleicher & Schuell paper filter No. 595), washed extensively with water and the filtrate was evaporated on a rotary evaporator (Buechi, Rotavapor RE). The desired deblocked peptide is in the residue.

B. Synthesis of the pentapeptide Tyr-Pro-Phe-Pro-Gly-methyl ester (β-casomorphine-5-OMet)

Step 1: (a) Manufacture of the mixed anhydride (Z-Phe-Pro-mixed anhydride)

640 mg (1.6 mM; =6% surplus) of the dipeptide Z-L-Phe-L-Pro (whereby Z is a N-benzyloxycarbonyl residue, which acts as a protective group) are reacted in 20 ml dimethylformamide (DMF) with 200 μl (1.5 mM) chlorine-formic acid-isobutyl ester at −15° C. after adding 170 μl (1.6 mM) N-methylmorpholine, for 15 min.

(b) Preparation of the amino components 125.6 mg (1.0 mM) glycine methyl ester hydrochloride are dissolved in 20 ml DMF by adding 110 μl (1 mM) N-methylmorpholine at −15° C.

Step 2: Conversion of the mixed anhydride of Step 1a with the amino component 1b. The Z-Phe-Pro-mixed anhydride is converted with the glycine methyl ester in 40 ml DMF at −15° C. for 4 hours.

Z-Phe-Pro-mixed anhydride+Gly-metester
−15° C./4 h Z-Phe-Pro-Gly-metester.

Prior to processing the 50% surplus of mixed anhydride is destroyed. At 0° C. the pH of the reaction product is brought to pH 2 with an aqueous saturated KHCO₃ solution and stirred for 30 min at 0° C. After this the peptide is extracted with 50 to 100 ml ethyl acetate (EtAc), and the EtAc-peptide mixture is washed with a saturated aqueous sodium chloride solution. After a further final washing with water the EtAc-phase is evaporated.

Step 3: The protective group is split-off by hydration. The peptide is dissolved in 30 ml methanol, and 100 mg paladium on activated carbon (Merck) are added. After replacing the air with nitrogen, hydrogen is added to the reaction container. The hydration is carried out at 25° C. to 30° C. The hydration is finished when no $CO_2$ is released, that is, when after checking with an aqueous barium hydroxide solution, a precipitate is no longer formed. The solution is filtered, washed with water, and rotated in the rotary evaporator. This remaining intermediate product is then used in Step 4 as the amino component.

Step 4 (a) Manufacture of the mixed anhydride (Z-Pro-mixed anhydride).

374 mg (1.5 mM) Z-L-Proline are dissolved in 15 ml DMF by adding 170 μl (1.5 mM) N-methylmorpholine and converted with 180 μl (1.4 mM) of chlorine-formic acid-isobutyl ester at −15° C. in 15 min.

(b) Conversion of the mixed anhydride from Step 4a with the amino component of Step 3. Z-L-Pro-anhydride+Phe-Pro-Gly-metester (in 15 ml DMF) −15° C./4 hrs Z-Pro-Phe-Pro-Gly-metester.

The destruction of the excess mixed anhydride, the extraction steps, and the hydration are carried out exactly as described before. The end product 4b serves as amino component for Step 5. A check of the amino acid composition after the hydrolysis resulted in the correct molar amino acid relation of this peptide. A test of the opiate activity (testing method see Example I) did not result in any opiate-like activity.

Step 5, (a) Formation of the mixed anhydride (Z-Tyr mixed anhydride)

629.24 (1.4 mM) N,O-di-Z-L-tyrosine are dissolved in 15 ml DMF by adding 165 μl (1.4 mM) N-methylmorpholine and converted with 175 μl (1.3 mM) chlorine-formic acid-isobutyl ester at −15° C. in 15 minutes.

(b) Conversion of the mixed anhydride from Step 5a with the end product of Step 4b. The end product of Step 4b is dissolved in 15 ml DMF and converted with the mixed anhydride of Step 5a at −15° C. in four hours. The destruction of the surplus mixed anhydride, the extraction and the hydration take place as described above.

The desired end product Tyr-Pro-Phe-Pro-Gly-methyl ester shows a strong specific opiate-like activity in the guinea pig intestine preparation. A splitting of the reaction products via Biogel P 2 (as described before) resulted in a defined position of the opiate activity.

After an acid hydrolysis was carried out the amino acid analysis resulted in a correct molar amino acid ratio corresponding to β-casomorphine-5. We would like to point out that the activation of the opiate active tetrapeptide (Step 4b) by means of tyrosine bonding to an opiate active peptide represents proof of the successful synthesis.

We claim:

1. Pharmacologically active peptides of the following formulas:

Tyr-Pro-A,
Tyr-Pro-A-Pro,
Tyr-Pro-A-Pro-B,
Tyr-Pro-A-Pro-B-Pro,
Tyr-Pro-A-Pro-B-Pro-C,
Tyr-Pro-A-Pro-B-Pro-C-Pro and
Tyr-Pro-A-Pro-B-Pro-C-Pro-D wherein A represents phenylalanine and tyrosine;

B represents glycine and tyrosine;

C represents isoleucine, proline and tyrosine;

D represents asparagine, proline and isoleucine;

and wherein (a) the end-positioned tyrosine has the general formula

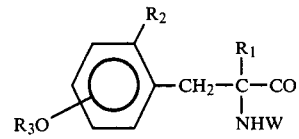

in which $R_1$ is hydrogen or an alkyl group with 1 to 4 C-atoms, $R_2$ is hydrogen or together with $R_1$ form an ethylene bond, $R_3$ is hydrogen, an alkyl group with 1 to 4 C-atoms or a $R_4CO$-group wherein $R_4$ is a saturated or unsaturated straight or branched chain alkyl residue with 1 to 17 C-atoms, a pheny residue or a phenylalkyl residue with 7 to 12 C-atoms, in which the phenyl residues can be substituted by 1 or 2 substituents of the halogen series, alkyl with 1 to 4 C-atoms or alkoxy with 1 to 4 C-atoms, in which the $R_3O$ group is in metal or para position to

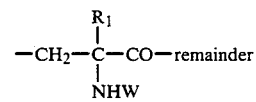

in which

W represents hydrogen, alkyl with 1 to 5 C-atoms, alkenyl with 3 to 5 C-atoms, cyclopropylmethyl, cyclobutylmethyl, $R_4CO$-, H-Arg, H-Lys-, H-Phe-, or H-Tyr-;

(b) the phenylalanine has the general formula

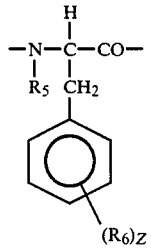

in which
R$_5$ represents hydrogen or alkyl with 1 to 4 C-atoms,
R$_6$ represents hydrogen, fluorine, chlorine, bromine, nitro, alkyl with 1 to 4 C-atoms or alkoxy with 1 to 4 C-atoms, and Z is 1 or 2;
(c) the proline has the general formula

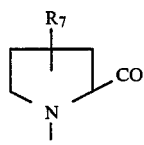

in which
R$_7$ represents hydrogen, a hydroxy group, an alkyl group or alkoxy group with 1 to 4 C-atoms;
an alkyl group or alkoxy group with 1 to 4 C-atoms is bonded at the nitrogen, and one or more keto groups are positioned on the ring; and
(d) the end-positioned, C-terminal amino acid is present as an amide or ester.

2. The method of treating a mammal suffering from pain which comprises administering to said animal an effective analgesic amount of a compound of claim 1.

3. A pharmacologically active peptide according to claim 1 having the formula Tyr-Pro-Phe-Pro-Gly-Pro-Ile.

4. A pharmacologically active peptide according to claim 1 having the formula Tyr-Pro-Phe-Pro-Gly.

5. A pharmacologically active peptide according to claim 1 having the formula Tyr-Pro-Phe-Pro.

6. A pharmacologically active peptide according to claim 1 having the formula Tyr-Pro-Phe.

7. A pharmacologically active peptide according to claim 1 having the formula Tyr-Pro-Phe-Pro-Gly-OMet.

8. A pharmacologically active peptide according to claim 1 having the formula Tyr-Pro-Phe-Pro-Gly-Pro.

9. Pharmacologically active peptides of the following formula in which the amino acids are D,L; L or D:
Tyr-Pro-A-Pro, wherein A represents phenylalanine; and wherein
(a) the end-positioned tyrosine present is of the general formula

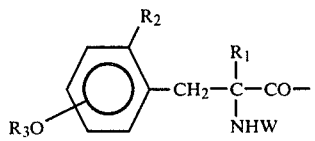

wherein the individual meaning is:
R$_1$ for hydrogen or an alkyl group with 1 to 4 C-atoms,
R$_2$ for hydrogen,
R$_3$ for hydrogen,
wherein W represents hydrogen, alkyl with 1 to 5 C-atoms, alkenyl with 3 to 5 C-atoms,
(b) the phenylalanine is of the general formula

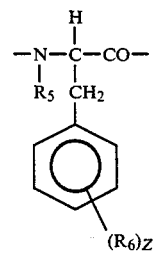

in which:
R$_5$ represents hydrogen or alkyl with 1 to 4 C-atoms,
R$_6$ represents hydrogen, alkyl with 1 to 4 C-atoms, and Z is 1
(c) proline of the general formula

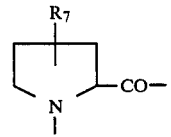

in which R$_7$ represents hydrogen, or a hydroxy group, and
(d) the end-positioned, C-terminal amino acid is present as an amide or ester.

10. A pharmaceutical composition for use as an analgesic comprising an analgesic effective amount of a compound of claim 9.

11. The method of treating a mammal suffering from pain which comprises administering to said mammal an effective analgesic amount of a compound of claim 9.

* * * * *